(12) United States Patent
Donnola et al.

(10) Patent No.: US 11,459,303 B2
(45) Date of Patent: Oct. 4, 2022

(54) PROCESS FOR THE SYNTHESIS OF LOFEXIDINE

(71) Applicant: Procos S.P.A., Cameri (IT)

(72) Inventors: Monica Donnola, Novara (IT); Alessandro Barozza, Nosate (IT); Jacopo Roletto, Turin (IT); Paolo Paissoni, Druento (IT)

(73) Assignee: Procos S.P.A., Cameri (IT)

( * ) Notice: Subject to any disclaimer, the term of this patent is extended or adjusted under 35 U.S.C. 154(b) by 0 days.

(21) Appl. No.: 17/617,598

(22) PCT Filed: Jun. 19, 2020

(86) PCT No.: PCT/EP2020/067105
§ 371 (c)(1),
(2) Date: Dec. 9, 2021

(87) PCT Pub. No.: WO2020/254580
PCT Pub. Date: Dec. 24, 2020

(65) Prior Publication Data
US 2022/0204455 A1    Jun. 30, 2022

(30) Foreign Application Priority Data
Jun. 21, 2019    (IT) .................. 102019000009777

(51) Int. Cl.
*C07D 233/22*    (2006.01)
(52) U.S. Cl.
CPC .................. *C07D 233/22* (2013.01)

(58) Field of Classification Search
None
See application file for complete search history.

(56) References Cited

U.S. PATENT DOCUMENTS 4,443,464 A    4/1984 Biedermann et al.

FOREIGN PATENT DOCUMENTS

| | | |
|---|---|---|
| EP | 0081748 A2 | 6/1983 |
| WO | 2009003868 A2 | 1/2009 |

OTHER PUBLICATIONS

Search Report and Written Opinion of PCT/EP2020/067105 dated Sep. 23, 2020.

*Primary Examiner* — Samantha L Shterengarts
(74) *Attorney, Agent, or Firm* — Silvia Salvadori, P.C.; Silvia Salvadori

(57) ABSTRACT

Disclosed is a process for the synthesis of lofexidine of formula (I) and the hydrochloride salt thereof (II), from ethyl 2-(2,6-dichlorophenoxy)propionate (III) and ethylenediamine in the presence of tetravalent titanium alkoxides, preferably titanium isopropoxide, in an apolar solvent such as toluene. A further object of the present invention is a process for the preparation of the intermediate ethyl 2-(2,6-dichlorophenoxy)propionate (III) from 2,6-dichlorophenol and ethyl 2-chloropropionate in the presence of a polar aprotic solvent and an alkali or alkaline earth carbonate salt, preferably potassium carbonate. Both processes are more cost-effective and more easily industrially scalable than the known procedures, thus enabling the active ingredient to be obtained with high yields at a limited cost.

16 Claims, 1 Drawing Sheet

Figure 1
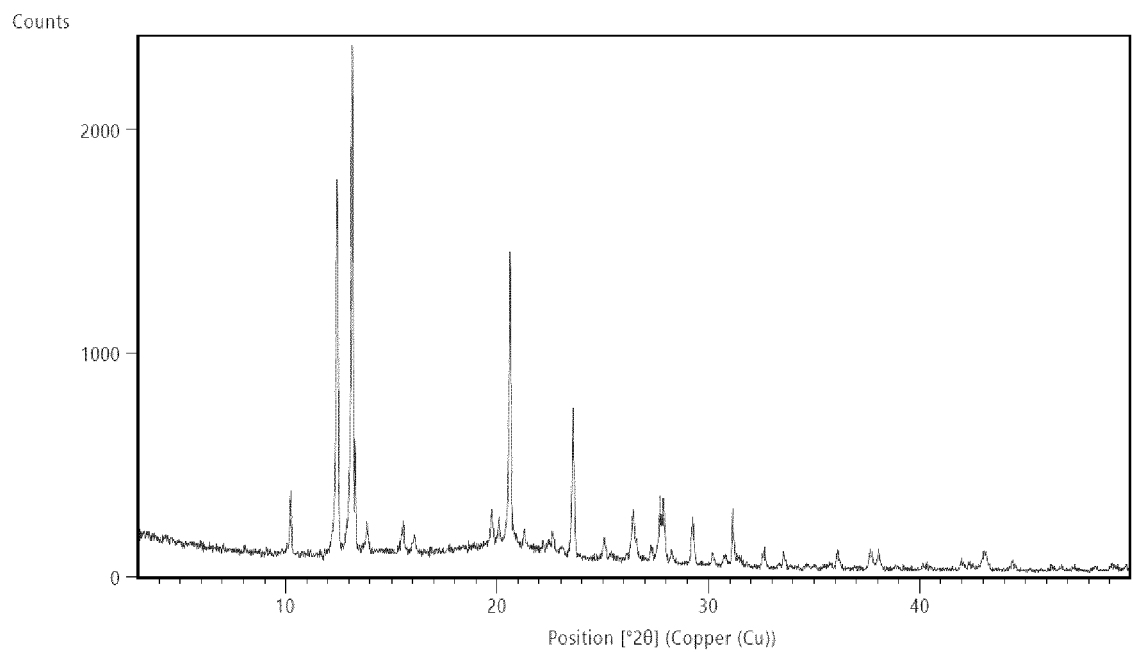
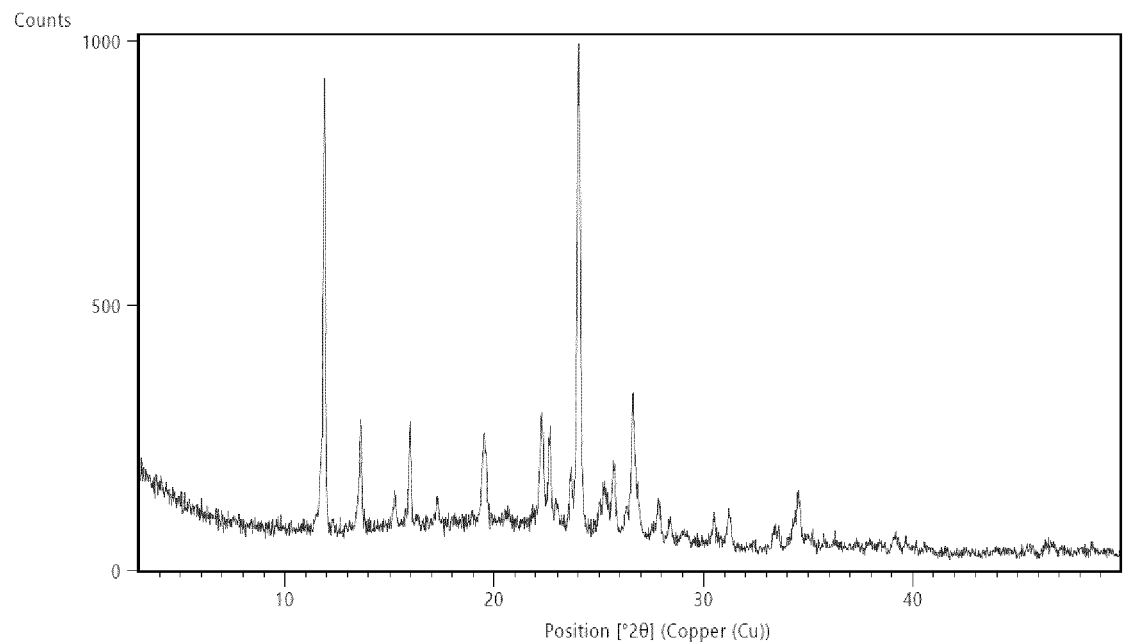
Figure 2

PROCESS FOR THE SYNTHESIS OF LOFEXIDINE

This application is a U.S. national stage of PCT/EP2020/067105 filed on 19 Jun. 2020, which claims priority to and the benefit of Italian Patent Application No. 102019000009777 filed on 21 Jun. 2019, the contents of which are incorporated herein by reference in their entireties.

The present invention relates to a process for the preparation of lofexidine (I), the hydrochloride salt thereof (II), and the intermediate ethyl 2-(2,6-dichloro-phenoxy)propionate (III).

BACKGROUND TO THE INVENTION

Lofexidine is an antihypertensive medicament which is currently most commonly used to treat the physical and psychological symptoms of opioid dependence. Structurally similar to clonidine, it is an alpha 2 adrenergic receptor agonist which acts by reducing norepinephrine release and moderating the symptoms of noradrenergic hyperactivity triggered by opioid withdrawal. Lofexidine and the hydrochloride salt thereof are represented by formulae (I) and (II).

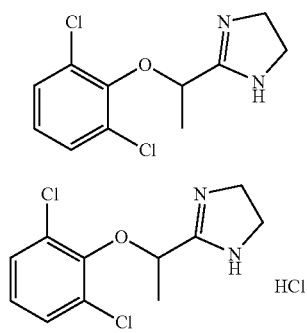

A limited number of synthesis strategies for the preparation of lofexidine (I) and the hydrochloride salt thereof (II) are known; they are mainly multi-step reactions wherein the product is always obtained with low yields starting with expensive reagents which are critical during use or difficult to obtain on the market.

U.S. Pat. No. 3,966,757 discloses a multi-step process for the preparation of lofexidine (I) and its hydrochloride (II) from 2,6-dichlorophenol and 2-bromopropionitrile, a very expensive reagent which is difficult to obtain, the reaction whereof gives rise to the formation of the intermediate 2-(2,6-dichlorophenoxy)propionitrile in a 70% yield which, following treatment with hydrochloric ethanol and ethylenediamine, gives the product with total yields below 50%. Said synthesis method is therefore inefficient and not cost-effective.

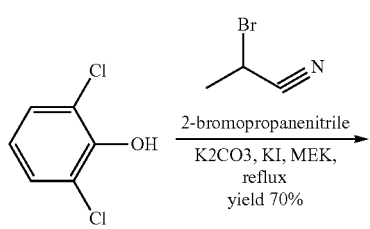

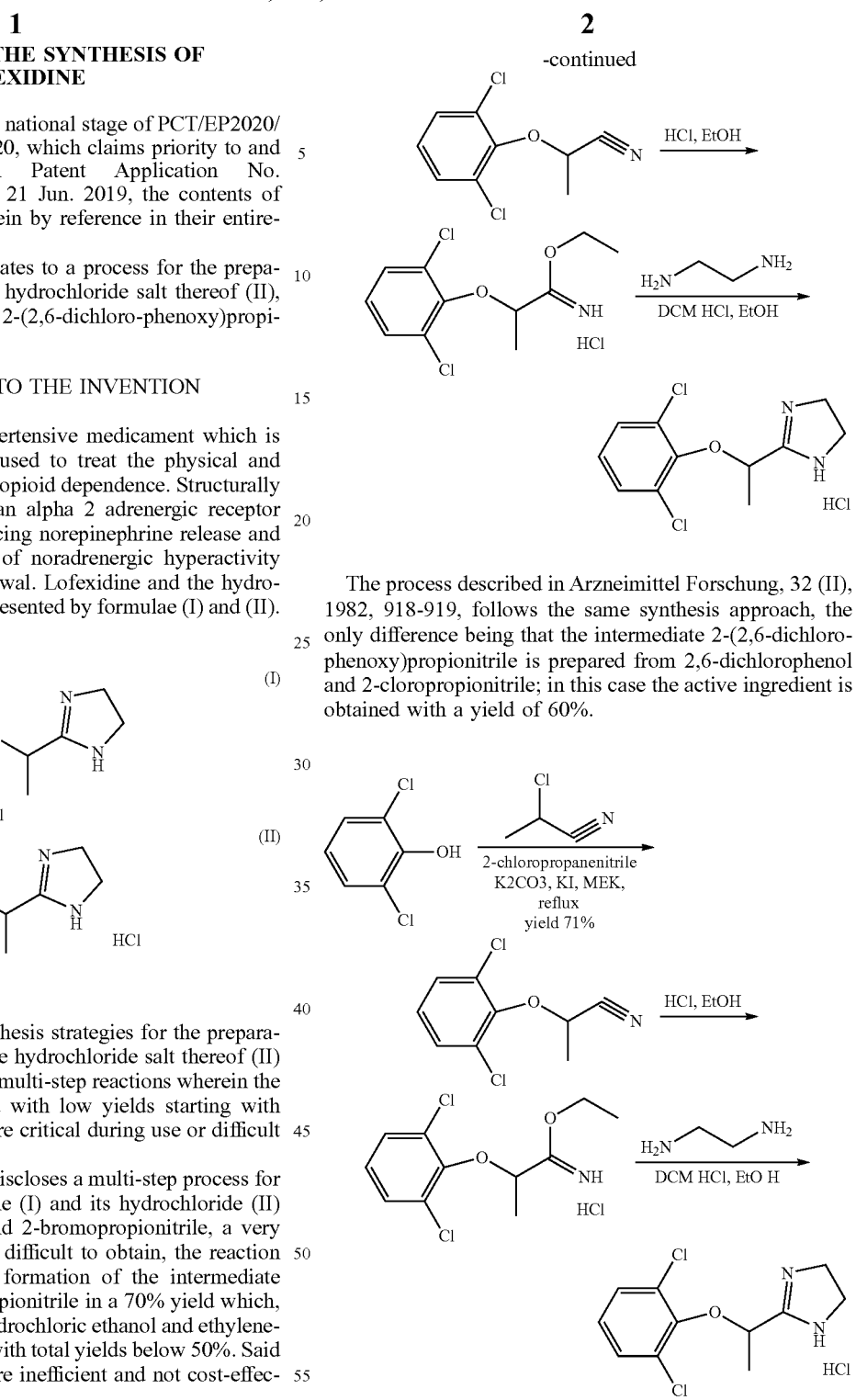

The process described in Arzneimittel Forschung, 32 (II), 1982, 918-919, follows the same synthesis approach, the only difference being that the intermediate 2-(2,6-dichlorophenoxy)propionitrile is prepared from 2,6-dichlorophenol and 2-cloropropionitrile; in this case the active ingredient is obtained with a yield of 60%.

WO2009003868 describes a different process which initially involves synthesis from the intermediate ethyl 2-(2,6-dichlorophenoxy)propionate (III), obtained in short times (1 h) and with quantitative yields (100%), by nucleophilic substitution from a haloethyl propionate through the use of carbonates such as caesium carbonate, in acetonitrile at room temperature. Ethyl 2-(2,6-dichloro-phenoxy)propionate (III) is then reacted in the presence of 2 equivalents of ethylenediamine and 2 equivalents of trimethylaluminum in toluene under reflux.

Although, unlike the procedure previously described, this process provides lofexidine in short times and with high yields (>90%), it is highly disadvantageous from the economic standpoint as it involves the use of caesium carbonate and trimethylaluminum, both of which reagents are expensive and difficult to obtain. The use of trimethylaluminum, which reacts violently with water, generating methane, makes the process difficult to apply on an industrial scale.

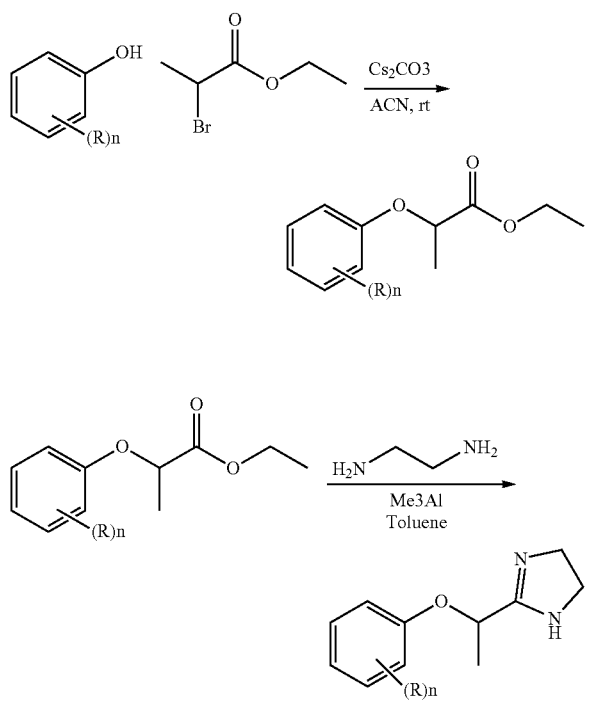

When attempting to reproduce the process disclosed in WO 2009003965, the Applicant did not obtain a quantitative conversion to lofexidine (I), but found in the reaction mixture the product of degradation (5-(2,6-dichlorophenoxy)-6-methyl-1,2,3,6-tetrahydropyrazine) of formula:

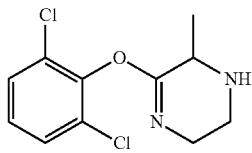 [SMILES: CC1NCCN=C1Oc1c(Cl)cccc1Cl]

Said method therefore presents formation/degradation kinetics that limit its industrialisation, requiring reaction times of a few minutes to isolate the product in useful yields.

Apart from the process described in WO2009003868, the other known processes for preparation of the intermediate ethyl 2-(2,6-dichlorophenoxy)propionate (III) always produce low yields, never exceeding 50-60%.

In DE3149009, intermediate (III) is obtained by a nucleophilic substitution reaction from 2,6-dichlorophenol and ethyl 2-chloropropionate in the presence of potassium methoxide, using methyl ethyl ketone as solvent under reflux for 48 hours. The intermediate is obtained with a yield of 56%.

In U.S. Pat. No. 4,443,464, ethyl 2-(2,6-dichlorophenoxy) propionate (III) is prepared by the same synthesis process, but using potassium ethoxide instead of potassium methoxide, and again provides low yields (56%).

DESCRIPTION OF THE INVENTION

It has been found that lofexidine (I) can be obtained with high yields and high purity, without the formation of degradation products, even at residence times long enough to allow the application of the process on an industrial scale (up to 18 hours under reflux), if the racemic intermediate ethyl 2-(2,6-dichlorophenoxy)propionate (III) is reacted with ethylenediamine in the presence of titanium isopropoxide in toluene.

It has also been found that the racemic intermediate ethyl 2-(2,6-dichlorophenoxy)propionate (III) can be obtained with high yields and cost- effectively by starting with 2,6-dichlorophenol and ethyl 2-chloropropionate in the presence of potassium carbonate in a polar aprotic solvent.

The invention therefore relates to a process for the preparation of lofexidine base or hydrochloride which comprises:

a) reacting 2,6-dichlorophenol and ethyl 2-chloropropionate in a polar aprotic solvent in the presence of an alkali metal carbonate to give ethyl 2-(2,6-dichlorophenoxy)propionate of formula (III)

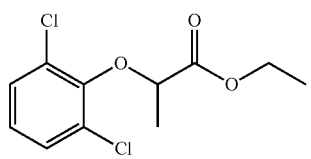

b) reacting the compound of formula (III) with ethylenediamine in the presence of tetravalent titanium alkoxides, in an apolar solvent.

The process according to the invention, shown in the scheme below, has various advantages over the known processes.

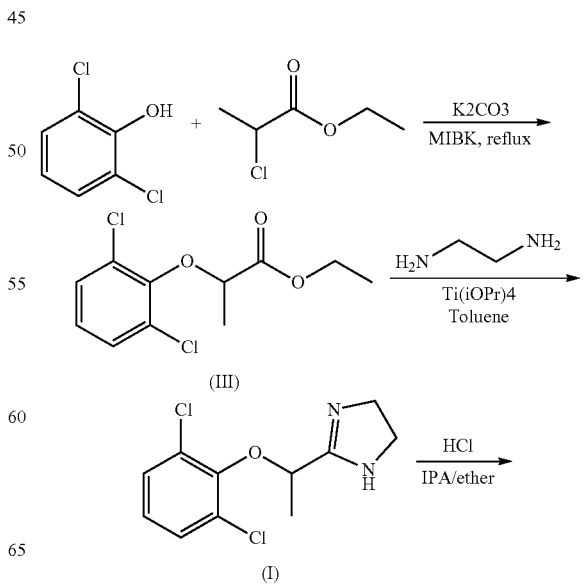

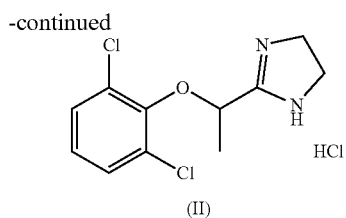

(II)

The use of titanium alkoxide in toluene produces the active ingredient with high yields and cost-effectively, as titanium alkoxide is cheaper than trimethylaluminum.

The process according to the invention is not only more cost-effective but also easily industrially scalable because it avoids the use of a pyrophoric reagent such as trimethylaluminum, replacing it with titanium alkoxide, and is highly selective in forming lofexidine (I) compatibly with large-scale implementation times, preventing its degradation to (5-(2,6-dichlorophenoxy)-6-methyl-1,2,3,6-tetrahydropyrazine).

In step a), although potassium carbonate is less soluble in organic solvents than caesium carbonate, its use produces intermediate (III) with high yields (>90%) and more cost-effectively, as potassium carbonate is a much cheaper reagent than caesium carbonate and is widely available.

The process according to the invention therefore yields both the intermediate ethyl 2-(2,6-dichlorophenoxy)propionate (III) and lofexidine (I) and the hydrochloride salt thereof (II) in a much more efficient, cost-effective and easily industrially scalable way.

DETAILED DESCRIPTION OF THE INVENTION

The preparation of ethyl 2-(2,6-dichlorophenoxy)propionate (III) comprises reacting 2,6-dichlorophenol in solid form, either melted or in solution in 2-20 volumes of reaction solvent, preferably in solution in 5-10 volumes, with ethyl 2-chloropropionate, either neat or in solution in up to 20 volumes of reaction solvent, preferably in the absence of solvent.

The reaction is conducted in a polar aprotic solvent such as acetone, DMF, methyl ethyl ketone or methyl isobutyl ketone, preferably methyl isobutyl ketone, which allows a fast work-up by adding water, which leads to the dissolution of inorganic salts allowing quantitative recovery of intermediate (III) in the organic phase.

The reaction is conducted in the presence of a carbonate, preferably selected from potassium carbonate and sodium carbonate, in stoichiometric amounts or higher, ranging between 1 and 5 equivalents, preferably between 1 and 2 equivalents.

According to an optimised version, step a) is conducted as follows. The order in which the reagents are added may differ from that reported below.

Typically, 1 mole of 2,6-dichlorophenol is reacted with 1-5 moles of potassium or sodium carbonate, preferably 1-1.4 moles, and with 1-5 moles of ethyl-2-chloropropionate, preferably 1-1.4 moles, in the presence of a polar aprotic solvent, preferably methyl isobutyl ketone, under reflux.

When the reaction has terminated, the reaction mixture containing ethyl 2-(2,6-dichlorophenoxy)propionate (III) is brought to the temperature of 0-40° C., preferably 15-25° C., and water is added. The biphasic mixture is separated, and the organic phase is washed with basic solutions, saline and water. The mixture is concentrated to residue, under vacuum, at a temperature ranging between 25° C. and 90° C., preferably at 40-50° C., and the resulting high-purity (>95%) oil is used neat in the next step.

The use of potassium and sodium carbonate, which are cheaper than caesium carbonate, combined with polar aprotic solvents at high temperatures, quantitatively promotes the formation of ethyl 2-(2,6-dichlorophenoxy)propionate (III) with high degrees of purity.

Step b) is conducted by reacting ethyl 2-(2,6-dichlorophenoxy)propionate (III), either neat or in solution in the reaction solvent in 1-20 volumes, preferably 1-10 volumes, and ethylenediamine in amounts of 1-20 equivalents, preferably 1.2-2 equivalents, with respect to ethyl 2-(2,6-dichlorophenoxy)propionate (III), either neat or in solution in up to 20 volumes of reaction solvent, preferably 1-5 volumes.

The reaction is conducted in apolar solvents such as THF, alkanes, cycloalkanes and aromatic hydrocarbons, preferably toluene, which allows a fast work-up by adding water to dissolve the inorganic salts and recover lofexidine (I) almost quantitatively in the organic phase.

The reaction is conducted in the presence of tetravalent titanium alkoxides such as titanium methoxide, titanium ethoxide and titanium isopropoxide, preferably titanium isopropoxide, in stoichiometric amounts or higher, ranging between 1 and 5 equivalents, preferably between 1.2 and 2 equivalents.

Lofexidine hydrochloride (II) is obtained by dissolving or suspending the base in apolar alcohol-based solvents or mixtures of alcohol-based solvents and ethers under heating, saturating the system with HCl and isolating the product after cooling, and optionally adding an anti-solvent (ethers or ketones miscible with the solvent).

According to an optimised version, step b) is conducted as follows. The order in which the reagents are added may differ from that reported below.

Typically, 1 mole of ethyl 2-(2,6-dichlorophenoxy)propionate (III) is reacted with 1-2 moles of titanium isopropoxide, in particular 1.5 moles, and with 1-2 moles of ethylenediamine, in particular 1.5 moles, in the presence of an apolar solvent, preferably toluene, under heating, preferably at 110° C.

The reaction is controlled by UPLC analysis, typically using an ACQUITY UPLC® BEH C18 column, 1.7 μm, 2.1×50 mm, with a water/acetonitrile/0.1% formic acid mixture as eluent phase.

When the reaction has terminated, the reaction mixture containing lofexidine (I) is brought to the temperature of 0-40° C., preferably 15-25° C., and an aqueous solution of 1%-50%, preferably 30%, tartaric acid is added. The biphasic mixture containing the titanium compounds is dissolved by adding a 1%-35%, preferably 30%, aqueous solution of NaOH, the phases are separated, and the organic phase is washed with saline solutions and water.

The mixture is concentrated to residue, under vacuum, at a temperature ranging between 25° C. and 90° C., preferably at 40-50° C., and the resulting high-purity (>95%) solid is used neat in the next step) or, if necessary, purified by crystallisation or trituration from aprotic solvents, preferably hexane, heptane, methyl isobutyl ketone or methyl ethyl ketone (XPRD in FIG. 1).

Lofexidine hydrochloride (II) is preferably obtained by dissolving the base in alcohol-based solvents, preferably isopropanol, under heating, saturating the system with HCl or a solution of HCl in alcohol and isolating the product after cooling, and optionally adding an anti-solvent (ethers or ketones, preferably diethyl ether). The X-ray diffractogram of the hydrochloride is shown in FIG. 2.

During the lofexidine HCl (II) preparation process, it was found that even when the hydrochloride salt is precipitated from different mixtures of solvents, the resulting crystal presents a diffractogram not yet described in the literature, shown in FIG. 2.

The object of the invention is therefore the crystalline hydrochloride of lofexidine having the following peaks on the XRPD spectrum recorded under the following conditions: PAN Analytical X'Pert Pro 45 KVolt, 40 mA, PAN Analytical XRD X'Pert tube—LFF (Long fine focusing). Radiation: Cu target with 2 Beryllium windows. Range (2Theta): 2°-50°).

| Pos. [°2θ] | Height [cts] | FWHM Left [°2θ] | d-spacing [Å] | Rel. Int. [%] |
| --- | --- | --- | --- | --- |
| 11.8725 | 553.95 | 0.1167 | 7.44816 | 80.87 |
| 13.5898 | 118.31 | 0.1596 | 6.51057 | 17.27 |
| 15.9615 | 133.40 | 0.1023 | 5.54811 | 19.47 |
| 19.5122 | 127.64 | 0.2079 | 4.54576 | 18.63 |
| 22.2457 | 155.02 | 0.1894 | 3.99298 | 22.63 |
| 22.6346 | 126.01 | 0.1374 | 3.92524 | 18.40 |
| 23.6493 | 75.81 | 0.1074 | 3.75908 | 11.07 |
| 24.0229 | 685.00 | 0.1569 | 3.70146 | 100.00 |
| 25.6996 | 97.69 | 0.1700 | 3.46363 | 14.26 |
| 26.6275 | 180.23 | 0.1808 | 3.34500 | 26.31 |

The invention will now be illustrated in detail by the following examples.

Synthesis of (+/−) ETHYL 2-(2,6-DICHLOROPHENOXY)PROPIONATE (III)

EXAMPLE 1

Powdered $K_2CO_3$ (59.3 g, 0.429 moles) and MIBK (150 ml, 3 volumes) are loaded at room temperature into a 100 mL reactor rendered inert with $N_2$. A solution of 2,6-dichlorophenol (50 g, 0.307 moles) in MIBK (150 ml, 3 volumes) is added to the suspension. The suspension is stirred at room temperature for 10-15 minutes, and ethyl 2-chloropropionate (58.5 g, 54.6 ml, 0.429 moles) is then added slowly. The suspension is heated under reflux temperature (116° C.) for 5 h. The reaction is complete after 5 h: >99% conversion to ethyl 2-(2,6-dichlorophenoxy)propionate. The suspension is left to stand at room temperature, and the salts are dissolved by adding $H_2O$ (150 ml, 3 volumes). The phases are separated and the aqueous phase is washed with MIBK (150 ml, 3 volumes). The combined organic phases are washed with a 5% solution of aqueous NaOH (100 ml, 2 volumes), then with $H_2O$ (200 ml, 4 volumes) and finally concentrated to an oily residue by complete evaporation of the solvent. Yield >90%. Purity >95%.

EXAMPLE 2

Powdered $K_2CO_3$ (59.3 g, 0.429 moles) and MIBK (150 ml, 3 volumes) are loaded at room temperature into a 100 mL reactor rendered inert with $N_2$. A solution of 2,6-dichlorophenol (50 g, 0.307 moles) in MIBK (150 ml, 3 volumes) is added to the suspension. The suspension is stirred at room temperature for 10-15 minutes, and ethyl 2-chloropropionate (58.5 g, 54.6 ml, 0.429 moles) is then added slowly. The suspension is heated at the temperature of 60° C. for 36 h. The reaction is complete after 36 h: >99% conversion to ethyl 2-(2,6-dichlorophenoxy) propionate. The suspension is left to stand at room temperature, and the salts are dissolved by adding $H_2O$ (150 ml, 3 volumes). The phases are separated and the aqueous phase is washed with MIBK (150 ml, 3 volumes). The combined organic phases are washed with a 5% solution of aqueous NaOH (100 ml, 2 volumes), then with $H_2O$ (200 ml, 4 volumes) and finally concentrated to an oily residue by complete evaporation of the solvent. Yield >90%. Purity >95%.

EXAMPLE 3

Powdered $K_2CO_3$ (59.3 g, 0.429 moles) and MIBK (150 ml, 3 volumes) are loaded at room temperature into a 100 mL reactor rendered inert with $N_2$. A solution of 2,6-dichlorophenol (50 g, 0.307 moles) in MIBK (150 ml, 3 volumes) is added to the suspension. The suspension is stirred at room temperature for 10-15 minutes, and ethyl 2-chloropropionate (58.5 g, 54.6 ml, 0.429 moles) is then added slowly. The suspension is heated at the temperature of 80° C. for 24 h. The reaction is complete after 24 h: >99% conversion to ethyl 2-(2,6-dichlorophenoxy) propionate. The suspension is left to stand at room temperature, and the salts are dissolved by adding $H_2O$ (150 ml, 3 volumes). The phases are separated and the aqueous phase is washed with MIBK (150 ml, 3 volumes). The combined organic phases are washed with a 5% solution of aqueous NaOH (100 ml, 2 volumes), then with $H_2O$ (200 ml, 4 volumes), and finally concentrated to an oily residue by complete evaporation of the solvent. Yield >90%. Purity >95%.

EXAMPLE 4

$Na_2CO_3$ (45.47 g, 0.429 moles) and MIBK (150 ml, 3 volumes) are loaded at room temperature into a 100 mL reactor rendered inert with $N_2$. A solution of 2,6-dichlorophenol (50 g, 0.307 moles) in MIBK (150 ml, 3 volumes) is added to the suspension. The suspension is stirred at room temperature for 10-15 minutes, and ethyl 2-chloropropionate (58.5 g, 54.6 ml, 0.429 moles) is then added slowly. The suspension is heated under reflux temperature (116° C.) for 5 h. The reaction is complete after 5 h: >99% conversion to ethyl 2-(2,6-dichlorophenoxy) propionate. The suspension is left to stand at room temperature, and the salts are dissolved by adding $H_2O$ (150 ml, 3 volumes). The phases are separated and the aqueous phase is washed with MIBK (150 ml, 3 volumes). The combined organic phases are washed with a 5% solution of aqueous NaOH (100 ml, 2 volumes), then with $H_2O$ (200 ml, 4 volumes), and finally concentrated to an oily residue by complete evaporation of the solvent. Yield >90%. Purity >95%.

Synthesis of LOFEXIDINE (I)

COMPARATIVE EXAMPLE 5

Toluene (32 ml, 6.4 volumes) is loaded at room temperature into a 100 mL reactor rendered inert with $N_2$. The temperature is reduced to 0° C., and 2M trimethylaluminum in toluene (15.50 g, 38.49 mmols) is added. While maintaining said temperature, a solution of ethylenediamine (2.3 g, 38.40 mmols) in toluene (13.4 ml, 2.7 volumes) is added, exothermic reaction. At the end of the addition the mass is brought to RT, and stirred at said temperature for 1 h. The solution is cooled again to 0° C., and a solution of (+/−) ethyl 2-(2,6-dichlorophenoxy) propionate (5 g, 19 mmols) in toluene (20 ml, 4 volumes) is added slowly. The reaction mixture is stirred under reflux, 110° C. When 95% conversion to 5-(2,6-dichlorophenoxy)-6-methyl-1,2,3,6-tetrahydropyrazine is observed with a residue of 5% (+/−) ethyl 2-(2,6-dichlorophenoxy)propionate (after about 3 hours), the yellow solution is again cooled to 0° C., MeOH (9 ml) is added very slowly and, when fume formation has ended, $H_2O$ (20 ml, 4 volumes) is added, again at 0° C., thus precipitating the aluminum salts, which are removed by vacuum filtration. The solution is diluted with ethyl acetate (40 ml, 8 volumes), the phases are separated, and the aqueous phase is washed with further ethyl acetate (40 ml, 8 volumes). The combined organic phases are washed with $H_2O$ (40 ml, 8 volumes), and finally concentrated to residue by complete evaporation of the solvent, until a yellowish-white solid is obtained. Yield >86%. Lofexidine (I) is not obtained, but a different product, with 95% purity, of formula

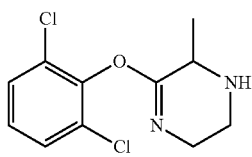 [SMILES: CC1NCCN=C1Oc1c(Cl)cccc1Cl]

$^1$H NMR (400 MHz, Chloroform-d) δ 7.42 (ddd, J=8.3, 6.8, 1.5 Hz, 2H Arom), 7.26 (t, J=8.1 Hz, 1H Arom), 4.19-3.91 (m, 4H, CH, $CH_2$, CH), 3.82-3.46 (m, 2H, CH, NH), 1.21 (d, J=6.6 Hz, 3H, $CH_3$).

EXAMPLE 6

Titanium isopropoxide (Ti(iOPr)$_4$) (5.4 g, 19 mmols) and toluene (30 ml, 6 volumes) are loaded at room temperature into a 100 mL reactor rendered inert with $N_2$. A solution of ethylenediamine (1.15 g, 19 mmols) in toluene (15 ml, 3 volumes) is then added. The reaction mixture is stirred at room temperature for 1 h, and a solution of (+/) ethyl 2-(2,6-dichlorophenoxy)propionate (5 g, 19 mmols) in toluene (20 ml, 4 volumes) is then added. The reaction mixture is stirred under reflux, 110° C. After 18 h under reflux, 97% conversion to lofexidine (I) is observed. The yellow-orange solution is diluted with 30% tartaric acid (50 ml, 10 volumes). The toluene phase is discarded, while the aqueous acid phase containing the titanium salts and the product as tartrate is diluted by adding further toluene (50 ml, 10 volumes), and the product is extracted in organic phase by adding 30% NaOH until pH 12 is reached. The phases are separated and the aqueous phase is washed twice more with toluene (25 ml×2; 2×5 volumes). The combined organic phases are washed with $H_2O$ (25 ml, 5 volumes), and finally concentrated to residue by complete evaporation of the solvent, until a yellowish-white solid is obtained.

Yield >90%. Purity >95%.

The resulting product can be used neat for precipitation as hydrochloride, or further purified by crystallisation with heptane or hexane, or by trituration at room temperature with methyl isobutyl ketone or methyl ethyl ketone. Purification yield 75-90% and purity >99%.

$^1$H NMR (400 MHz, Chloroform-d) δ 7.31 (d, J=8.1 Hz, 2H Arom), 7.01 (t, J=8.1 Hz, 1H Arom), 5.16 (q+s (broad), J=6.6 Hz, 2H, CH, NH), 3.65 (dd, J=25.5, 8.6 Hz, 4H, $CH_2$-$CH_2$), 1.59 (d, J=6.6 Hz, 3H, $CH_3$).

EXAMPLE 7

Titanium isopropoxide (Ti(iOPr)$_4$) (6.5 g, 22.8 mmols) and toluene (30 ml, 6 volumes) are loaded at room temperature into a 100 mL reactor rendered inert with $N_2$. A solution of ethylenediamine (1.40 g, 22.8 mmols) in toluene (15 ml, 3 volumes) is then added. The reaction mixture is stirred at room temperature for 1 h, and a solution of (+/) ethyl 2-(2,6-dichlorophenoxy) propionate (5 g, 19 mmols) in toluene (20 ml, 4 volumes) is then added. The reaction mixture is stirred under reflux, 110° C. The reaction is complete after a total of 18 h: 98% conversion to lofexidine (I). The yellow-orange solution is diluted with 30% tartaric acid (50 ml, 10 volumes). The toluene phase is discarded, while the aqueous acid phase containing titanium salts and the product as tartrate is diluted by adding further toluene (50 ml, 10 volumes), and the product is extracted in organic phase by adding 30% NaOH until pH 12 is reached. The phases are separated and the aqueous phase is washed twice more with toluene (25 ml×2; 2×5 volumes). The combined organic phases are washed with $H_2O$ (25 ml, 5 volumes), and finally concentrated to residue by complete evaporation of the solvent, until a yellowish-white solid is obtained. Yield >90%. Purity >95%.

The resulting product can be used neat for precipitation as hydrochloride, or further purified by crystallisation with heptane or hexane, or by trituration at room temperature with methyl isobutyl ketone or methyl ethyl ketone. Purification yield 75-90% and purity >99%.

$^1$H NMR: Conforming to the structure of lofexidine (I)

EXAMPLE 8

Titanium isopropoxide (Ti(iOPr)$_4$) (32.4 g, 0.114 moles) and toluene (120 ml, 6 volumes) are loaded at room temperature into a 500 ml reactor rendered inert with $N_2$. A solution of ethylenediamine (6.9 g, 0.114 moles) in toluene (54 ml, 3 volumes) is then added. The reaction mixture is stirred at room temperature for 1 h, and a solution of (+/) ethyl 2-(2,6-dichlorophenoxy) propionate (20 g, 0.076 moles) in toluene (80 ml, 4 volumes) is then added. The reaction mixture is stirred under reflux, 110° C. The reaction is complete after a total of 5 h: conversion >98% to give lofexidine (I).

The yellow-orange solution is diluted with 30% tartaric acid (200 ml, 10 volumes). The toluene phase is discarded, while the aqueous acid phase containing titanium salts and the product as tartrate is diluted by adding further toluene (200 ml, 10 volumes), and the product is extracted in organic phase by adding 30% NaOH until pH 12 is reached. The phases are separated and the aqueous phase is washed twice more with toluene (100 ml×2; 2×5 volumes). The combined organic phases are washed with $H_2O$ (100 ml, 5 volumes), and finally concentrated to residue by complete evaporation of the solvent, until a yellowish-white solid is obtained. Yield >90%. Purity >95%.

The resulting product can be used neat for precipitation as hydrochloride, or further purified by crystallisation with heptane or hexane, or by trituration at room temperature with methyl isobutyl ketone or methyl ethyl ketone. Purification yield 75-90% and purity >99%.

$^1$H NMR: Conforming to the structure of lofexidine (I)

Synthesis of LOFEXIDINE HCl (II)

EXAMPLE 9

Lofexidine (I) is dissolved in a mixture of diethyl ether/ethanol (9:1, 4 volumes). 37% HCl (1.1 equiv) is added drop by drop to the solution. The resulting suspension is stirred at room temperature, and diethyl ether (4 volumes) is added after 10 min. The white solid is filtered, washed with diethyl ether (2 volumes×3 times) and air dried (yield >90%).

The diffractogram of lofexidine HCl (II) is shown in FIG. 2 (diffractometer:PAN Analytical X'Pert Pro, 45 KVolt, 40 mA, equipped with PAN Analytical XRD X'Pert tube—LFF (Long fine focusing). Radiation: Cu target with 2 Beryllium windows. Range (2Theta): 2°-50°).

EXAMPLE 10

(+/−) lofexidine (I) is dissolved in isopropanol (4 volumes). Isopropanol HCl (4 volumes) is added drop by drop to the solution. The white solid is filtered and air dried (yield >60%).

XRPD: Conforming to the structure of lofexidine HCl (II).

EXAMPLE 11

Lofexidine (I) is dissolved in a mixture of diethyl ether/isopropanol (9:1, 10 volumes). 37% HCl (1.1 equiv) is added drop by drop to the solution. The resulting suspension is stirred at room temperature, and diethyl ether (10 volumes) is added after 10 min.

The white solid is filtered, washed with diethyl ether (5 volumes×3 times) and air dried (yield >90%).

XRPD: Conforming to the structure of lofexidine HCl (II).

EXAMPLE 12

Lofexidine (I) is dissolved in toluene (7 volumes). Isopropanol HCl is added drop by drop to the solution (until an acid pH is obtained). The white solid is filtered and air dried (yield >70%).

XRPD: Conforming to the structure of lofexidine HCl (II).

The invention claimed is:

1. A process for the preparation of lofexidine base or hydrochloride, which comprises:
   a) reacting 2,6-dichlorophenol and ethyl 2-chloropropionate in a polar aprotic solvent in the presence of an alkali metal carbonate to give ethyl 2-(2,6-dichlorophenoxy)propionate of formula (III)

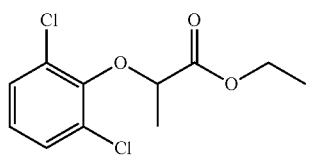

(III)

b) reacting the compound of formula (III) with ethylenediamine in the presence of tetravalent titanium alkoxides, in an apolar solvent.

2. The process according to claim 1 wherein the alkali metal carbonate is selected from sodium and potassium carbonate.

3. The process according to claim 1, wherein the polar aprotic solvent in step a) is selected from acetone, dimethylformamide, methyl ethyl ketone and methyl isobutyl ketone, or mixtures thereof.

4. The process according to claim 1, wherein 1 molar equivalent of 2,6-dichlorophenol is reacted with 1-5 molar equivalents of potassium or sodium carbonate and with 1-5 molar equivalents of ethyl 2-chloropropionate.

5. The process according to claim 4, wherein 1 molar equivalent of 2,6-dichlorophenol is reacted with 1-1.4 molar equivalents of potassium or sodium carbonate and with 1-1.4 molar equivalents of ethyl 2-chloropropionate.

6. The process according to claim 1, wherein the tetravalent titanium alkoxides are selected from titanium methoxide, titanium ethoxide and titanium isopropoxide.

7. The process according to claim 1 wherein ethyl 2-(2,6-dichlorophenoxy)propionate (III) is reacted either neat or in solution in 1-20 volumes of reaction solvent with 1-20 equivalents of ethylenediamine, either neat or in solution in up to 20 volumes of reaction solvent.

8. The process according to claim 6 wherein the tetravalent titanium alkoxides are used in stoichiometric amounts or higher ranging from 1 to 5 equivalents.

9. The process according to claim 1 wherein the solvent of step b) is toluene.

10. The process according to claim 2 wherein the alkali metal carbonate is potassium carbonate.

11. The process according to claim 3, wherein the polar aprotic solvent in step a) is methyl isobutyl ketone.

12. The process according to claim 6, wherein the tetravalent titanium alkoxides is titanium isopropoxide.

13. The process according to claim 7, wherein ethyl 2-(2,6-dichlorophenoxy)propionate (III) is reacted either neat or in solution in 1-20 volumes of reaction solvent with 1.2-2 equivalents of ethylenediamine, either neat or in solution in up to 20 volumes of reaction solvent.

14. The process according to claim 7, wherein ethyl 2-(2,6-dichlorophenoxy)propionate (III) is reacted either neat or in solution in 1-20 volumes of reaction solvent with 1-20 equivalents of ethylenediamine, either neat or in solution in 1-5 volumes of reaction solvent.

15. The process according to claim 7, wherein ethyl 2-(2,6-dichlorophenoxy)propionate (III) is reacted either neat or in solution in 1-20 volumes of reaction solvent with 1.2-2 equivalents of ethylenediamine, either neat or in solution in 1-5 volumes of reaction solvent.

16. The process according to claim 8, wherein the tetravalent titanium alkoxides are used in amounts ranging from 1.2 to 2 equivalents.

* * * * *

UNITED STATES PATENT AND TRADEMARK OFFICE
CERTIFICATE OF CORRECTION

| | |
|---|---|
| PATENT NO. | : 11,459,303 B2 |
| APPLICATION NO. | : 17/617598 |
| DATED | : October 4, 2022 |
| INVENTOR(S) | : Monica Donnola et al. |

It is certified that error appears in the above-identified patent and that said Letters Patent is hereby corrected as shown below:

On the Title Page

Item (54) and In the Specification Column 1 Line 1:
-- PROCESS FOR THE SYNTHESIS OF LOFEXIDINE --
Should read:
"A PROCESS FOR THE SYNTHESIS OF LOFEXIDINE"

Signed and Sealed this
Seventeenth Day of January, 2023

Katherine Kelly Vidal
*Director of the United States Patent and Trademark Office*